United States Patent [19]

Gottlieb

[11] 4,006,220
[45] Feb. 1, 1977

[54] COMPOSITIONS AND METHODS USEFUL FOR REPAIRING DEPRESSED CUTANEOUS SCARS

[76] Inventor: Sheldon K. Gottlieb, 8708 Wandering Trail Drive, Potomac, Md. 20854

[22] Filed: June 4, 1975

[21] Appl. No.: 576,858

[52] U.S. Cl. .............................. 424/101; 424/177; 424/319
[51] Int. Cl.² ................ A61K 35/16; A61K 37/00; A61K 31/195
[58] Field of Search ........... 424/101, 177, 311, 319

[56] References Cited

UNITED STATES PATENTS

| | | | |
|---|---|---|---|
| 2,558,395 | 6/1951 | Studer | 424/177 |
| 3,632,350 | 1/1972 | Battista | 424/177 |

OTHER PUBLICATIONS

Weuffen, et al., *Chem. Abst.* vol. 71 (1969), p. 6522j.

*Primary Examiner*—Sam Rosen
*Attorney, Agent, or Firm*—Stanley D. Schwartz

[57] ABSTRACT

Compositions useful for the repair of depressed cutaneous scars comprising at least one fibrin stabilizer and plasma in an amount to provide sufficient fibrin within a cavity formed under the scar. The fibrin stabilizer or a mixture thereof is present in an amount effective to maintain the fibrin within the cavity and thereby cause the build-up of collagen within the cavity. A preferred composition comprises pulverized absorbable gelatin sponge and aminocaproic acid, or derivatives thereof, with plasma being used in combination thereof or permitted to flow naturally into the cavity immediately after the formation thereof. Methods for repairing depressed cutaneous scars including the step of introducing said compositions intradermally beneath the scar are also disclosed.

19 Claims, No Drawings

COMPOSITIONS AND METHODS USEFUL FOR REPAIRING DEPRESSED CUTANEOUS SCARS

BACKGROUND OF THE INVENTION

This invention relates to a method and compositions useful for the repair of depressed cutaneous scars such as those which are characteristic of acne vulgaris. More particularly, this invention relates to the use of at least one fibrin stabilizer in combination with plasma to achieve the desired results of this invention.

In the past, depressed cutaneous scars such as those associated with acne vulgaris have been treated by a number of techniques, the most notable of which is dermabrasion. This procedure is often excessively bloody and usually prolonged. In addition to waiting about 2 or more weeks for wound sites to heal and to evaluate the degree of success, it has been found that this procedure occasionally results in undesired pigmentary changes. Other techniques including such drawbacks include the incising and excising of the skin overlying the scar. Accordingly, a need therefore exists to eliminate these disadvantages and to provide a more efficient, beneficial and cosmetically acceptable process and composition useful for carrying out said process, for both the doctor and patient.

OBJECTS OF THE INVENTION

It is therefore a significant object of this invention to provide both a method and compositions useful for the repair of depressed cutaneous scars which overcome the disadvantages associated with previously known methods.

Another significant object of this invention is the provision of a new method for repairing depressed cutaneous scars which eliminates the need for surgical incisions or excisions.

A still further object of this invention is a method and composition capable of permanently repairing amenable depressed ovoid and linear lesions with immediate beneficial and cosmetically acceptable results without having to incise, excise or abrade the skin overlying the scar.

Still another object of this invention is the provision of a simple and efficient process and composition capable of enhancing tissue healing in a shorter period of time by the stabilization of fibrin which regulates connective tissue formation.

The invention will be better understood and objects other than those set forth above will become apparent after reading the following detailed description of preferred, yet illustrative, embodiments hereof.

BRIEF SUMMARY OF THE INVENTION

Briefly, the present invention relates to a composition useful for the repair of depressed cutaneous scars comprising at least one fibrin stabilizer and plasma. Another embodiment of this invention relates to a method for repairing depressed cutaneous scars comprising the step of introducing at least one fibrin stabilizer and plasma intradermally beneath a depressed scar.

DETAILED DESCRIPTION OF THE INVENTION

The fibrin stabilizer used in the practice of this invention can be any of the well known agents useful for the promoting of the build-up of fibrin in a given region. One such material is absorbable gelatin sponge which is a sterile, substantially water-insoluble, non-antigenic, completely proteolytically digestable pulverized gelatin sponge. A process for preparing absorbable gelatin sponge is disclosed in U.S. Pat. No. 2,464,357. This particular fibrin stabilizer functions as a stabilizer by trapping fibrin and fibrin precursors after being introduced intradermally beneath a depressed scar thereby significantly enhancing the build-up of new collagen tissue beneath said scar. In addition, this stabilizer also traps fibroblasts which replace fibrin to build the desired tissue up to the normal level.

Another useful fibrin stabilizer are those agents capable of inhibiting both plasmin activity and plasminogen activators which are responsible for the dissolution of newly formed fibrin and include aminocaproic acid (6-aminohexanoic acid) of the formula $NH_2CH_2(CH_2)_4COOH$, compounds of the formula:

$$4NH_2CH_2(CH_2)_4COOH \cdot CaX_2$$

wherein X is halogen and preferably choride or bromide, and other similar functioning compounds. Aminocaproic acid is prepared in accordance with Japanese Patent Nos. 215,676 and 215,679.

According to a preferred embodiment of this invention, both the absorbable gelatin sponge and aminocaprocic acid are employed in an admixture although it is understood that each agent can be used individually.

The fibrin stabilizer is employed in combination with plasma which is preferably of human origin and preferably from the patient being treated in accordance with this invention. The plasma can be initially admixed with at least one fibrin stabilizer or the plasma can be permitted to flow into the cavity produced by the preliminary step of transecting the intradermal scar tissue under thee scar and the accompanying injury to said tissue thereby forming said cavity.

The amount of fibrin stabilizer used in combination with plasma introduced into said cavity is dependent upon the stabilizer(s) employed and the size of the cavity formed beneath the depressed cutaneous scars by the transecting step, but in any event is an amount sufficient to maintain a minimum amount of fibrin within said cavity thereby resulting in the build-up of collagen within said cavity and resulting in the permanent elevation of the depression to a more cosmetically acceptable level thereby producing a substantially more continuous skin surface that improves the cosmetic appearance of the patient.

Generally, the amount of proteolytically disgestable pulverized absorbable gelatin sponge employed in the practice of this invention is between about 20 and 50 mg., and preferably between about 30 and 40 mg. for each 0.3 to 0.5 c.c. of plasma introduced into the cavity. The amount of aminocaproic acid used is between about 12.5 and 75 mg., and preferably between about 30 and 40 mg. for each 0.3 to 0.5 c.c. of plasma introduced into said cavity. Best results are believed to be achieved when a mixture consisting of (1) from about 20 to 50 mg. of pulverized absorbable gelatin sponge and, (2) from about 12.5 to 75 mg. of aminocaproic acid is used for each 0.3 to 0.5 c.c. of plasma introduced into said cavity.

It is understood that most cavities formed beneath depressed cutaneous scars are by means of transecting intradermal tissue resulting in the formation of a cavity having a diameter of between about 3 and 5 millimeters. In achieving the desired results of this invention, usually between about 0.3 and 0.5 c.c. of plasma are introduced into a cavity having the aforementioned dimensions with a proportionally greater amount of plasma being introduced into a larger cavity.

It is further understood that the source of plasma is preferably from either a sample of blood originally obtained from the patient or from that plasma flowing into the cavity immediately after the formation thereof or from a combination of the two sources. It is the plasma fibrinogen and the thrombin located in the cavity of the injured tissue that reacts and ultimately results in the formation of fibrin which is replaced by fibroblasts that is required for the build-up of the new tissue resulting in the permanent elevation of the depression to the normal level.

When a plasma is used from a blood sample already removed from the patient, it is desirable to obtain said plasma by taking 15 c.c. of the patient's venous blood and mixing the same with 2.3 c.c. of ACD (anti-coagulant citrate dextrose) solution and thereafter centrifuging at 2000 revolutions per minute for 10 minutes. The clear plasma is then collected in a sterile test tube for its subsequent use.

Plasma obtained in this manner or by other conventional procedures, may be either used immediately in the practice of this invention or may be stored for future use, such as in a refrigerator, with conventional additives optionally being incorporated into said plasma to aid in the preservation thereof, which need not be removed for the subsequent use of the plasma in the practice of this invention.

It is understood that various modifications may be made in the invention without departing from the spirit or scope thereof. Accordingly, what is claimed is:

1. A composition useful for the repair of depressed cutaneous scars comprising at least one fibrin stabilizer and plasma in an amount to provide sufficient fibrin within a cavity formed under said scar and said fibrin stabilizer being present in an amount effective to maintain said fibrin within said cavity and thereby cause the build-up of collagen within said cavity.

2. The composition of claim 1 wherein said composition contains from about 0.3 to 0.5 c.c. of human plasma.

3. The composition of claim 2 wherein said fibrin stabilizer is (1) pulverized absorbable gelatin sponge, (2) aminocaproic acid, or (3) mixtures thereof.

4. The composition of claim 3 containing from about 20 to 50 mg. of said pulverized absorbable gelatin sponge for each 0.3 to 0.5 c.c. of plasma.

5. The composition of claim 3 containing from about 12.5 to 75 mg. of aminocaproic acid for each 0.3 to 0.5 c.c. of plasma.

6. The composition of claim 3 containing a mixture of said pulverized absorbable gelatin sponge and aminocaproic acid wherein said mixture consists of from 20 to 50 mg. of pulverized absorbable gelatin sponge and from 12.5 to 75 mg. of aminocaproic acid for each 0.3 to 0.5 c.c. of plasma.

7. In a method for repairing a depressed cutaneous scar comprising the step of introducing the composition of claim 1 intradermally beneath said scar.

8. The method of claim 7 comprising initially transecting the intradermal fibrous tissue beneath said scar thereby forming a cavity.

9. The method of claim 8 comprising introducing a sufficient amount of said composition to stimulate the formation of new tisue thereby resulting in the permanent elevation of the depression to the normal skin level.

10. The method of claim 8 comprising introducing said plasma into said cavity from injured body tissues forming said cavity.

11. The method of claim 8 which comprises introducing said plasma into said cavity from (1) injured body tissues forming said cavity, and (2) from an intradermal injection.

12. The method of claim 8 wherein said stabilizer is (1) pulverized absorbable gelatin sponge, (2) aminocaproic acid, or (3) mixtures thereof.

13. The method of claim 12 wherein said composition contains from about 20 to 50 mg. of said pulverized absorbable gelatin sponge for each 0.3 to 0.5 c.c. of plasma introduced into said cavity.

14. The method of claim 12 wherein said composition contains from 12.5 to 75 mg. of aminocaproic acid for each 0.3 to 0.5 c.c. of plasma introduced into said cavity.

15. The method of claim 12 wherein said stabilizer is a mixture of about 20 to 50 mg. of said pulverized absorbable gelatin sponge and about 12.5 to 75 mg. of aminocaproic acid for a cavity having from about 0.3 to 0.5 c.c of plasma introduced therein.

16. The method of claim 7 comprising introducing about 0.3 to 0.5 c.c. of plasma into said cavity wherein said cavity has a diameter of between about 3 and 5 millimeters.

17. A composition useful for the repair of depressed cutaneous scars comprising:
 a. pulverized absorbable gelatin sponge, and
 b. a member selected from the group consisting of aminocaproic acid, compounds of the formula
 $4NH_2CH_2(CH_2)_4COOH.CaX_2$
 wherein X is halogen, and mixtures thereof,
 wherein said components (a) and (b) are both present in an amount sufficient to maintain fibrin within a cavity formed under said scar and thereby cause the build-up of collagen within said cavity.

18. The composition of claim 17 wherein (b) is aminocaproic acid.

19. The composition of claim 18 containing from 20 to 50 mg. of (a) and from 12.5 to 75 mg. of (b) for each 0.3 to 0.5 cc. of plasma entering said cavity.

* * * * *

UNITED STATES PATENT AND TRADEMARK OFFICE

CERTIFICATE EXTENDING PATENT TERM
UNDER 35 U.S.C. 156

Patent No.   : 4,006,220

Dated        : February 1, 1977

Inventor(s)  : Sheldon K. Gottlieb

Patent Owner : Sheldon K. Gottlieb

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

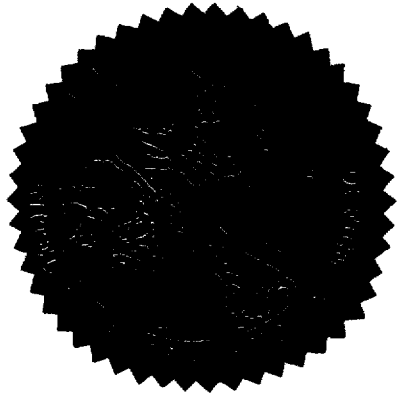

I have caused the seal of the Patent and Trademark Office to be affixed this Twenty-Third day of February 1989.

Donald J. Quigg

Assistant Secretary and Commissioner
of Patents and Trademarks